US011730393B2

(12) United States Patent
Stambeck

(10) Patent No.: US 11,730,393 B2
(45) Date of Patent: *Aug. 22, 2023

(54) DEVICE FOR COLLECTING PARTICLES IN AN EXHALED AIR FLOW

(71) Applicant: Munkplast AB, Uppsala (SE)

(72) Inventor: Peter Stambeck, Björklinge (SE)

(73) Assignee: MUNKPLAST AB, Uppsala (SE)

( * ) Notice: Subject to any disclaimer, the term of this patent is extended or adjusted under 35 U.S.C. 154(b) by 189 days.

This patent is subject to a terminal disclaimer.

(21) Appl. No.: 17/156,688

(22) Filed: Jan. 25, 2021

(65) Prior Publication Data
US 2021/0137415 A1 May 13, 2021

Related U.S. Application Data

(63) Continuation of application No. 15/856,090, filed on Dec. 28, 2017, now Pat. No. 10,898,108, which is a
(Continued)

(30) Foreign Application Priority Data

Jul. 1, 2015 (SE) .................................... 1550930-0

(51) Int. Cl.
A61B 5/097 (2006.01)
A61B 5/08 (2006.01)
G01N 33/497 (2006.01)
A61B 90/00 (2016.01)
A61B 5/091 (2006.01)
(Continued)

(52) U.S. Cl.
CPC .............. *A61B 5/097* (2013.01); *A61B 5/082* (2013.01); *A61B 5/091* (2013.01); *A61B 5/742* (2013.01); *A61B 5/7405* (2013.01); *A61B 10/00* (2013.01); *A61B 90/03* (2016.02); *G01N 1/2247* (2013.01); *G01N 33/497* (2013.01); *A61B 2010/0087* (2013.01); *A61B 2560/0285* (2013.01); *A61B 2560/0431* (2013.01); *G01N 2001/2223* (2013.01); *G01N 2001/2244* (2013.01)

(58) Field of Classification Search
None
See application file for complete search history.

(56) References Cited

U.S. PATENT DOCUMENTS 4,292,978 A 10/1981 Guth
5,787,884 A 8/1998 Tovey
(Continued)

Primary Examiner — Meredith Weare
(74) Attorney, Agent, or Firm — Reising Ethington P.C.

(57) ABSTRACT

A device for collecting aerosol particles in an exhaled air flow. The particles may be aerosol particles such as biomarkers or particles related to drugs or other substances formed or found in the alveoli of the lungs. The device comprises an elongate housing with an inner wall and at least four first type partition walls extending substantially perpendicularly from opposite sides of the inner wall to partly cover the cross-section of the housing. The first type partition walls create a labyrinth shaped flow path to divert air flowing from the inlet towards the outlet of the housing in a direction towards opposite inner walls of the housing so that the particles separate from the air flow and attach on the device. The distance between two opposite first type partition walls is smaller than the transverse width of the housing and increases in the flow direction.

16 Claims, 3 Drawing Sheets

Related U.S. Application Data continuation of application No. PCT/EP2016/064110, filed on Jun. 19, 2016.

(51) Int. Cl.
*A61B 5/00* (2006.01)
*A61B 10/00* (2006.01)
*G01N 1/22* (2006.01)

(56) References Cited

U.S. PATENT DOCUMENTS

| | | |
|---|---|---|
| 10,898,108 B2 * | 1/2021 | Stambeck ............... A61B 5/082 |
| 11,317,827 B2 * | 5/2022 | Stambeck ............. G01N 33/497 |
| 2003/0106556 A1 | 6/2003 | Alperovich et al. |
| 2004/0232052 A1 | 11/2004 | Call et al. |
| 2005/0204712 A1 | 9/2005 | Shekarriz et al. |
| 2006/0137689 A1 | 6/2006 | Evensson |
| 2008/0087347 A1 | 4/2008 | Truce et al. |
| 2009/0211210 A1 | 8/2009 | Engerran et al. |
| 2010/0297635 A1 | 11/2010 | Olin et al. |
| 2014/0024960 A1 | 1/2014 | Smith et al. |
| 2014/0366609 A1 | 12/2014 | Bo et al. |
| 2015/0033824 A1 | 2/2015 | Hammarlund et al. |
| 2018/0263531 A1 | 9/2018 | Stambeck |
| 2020/0268280 A1 * | 8/2020 | Stambeck ............... A61B 5/091 |

* cited by examiner

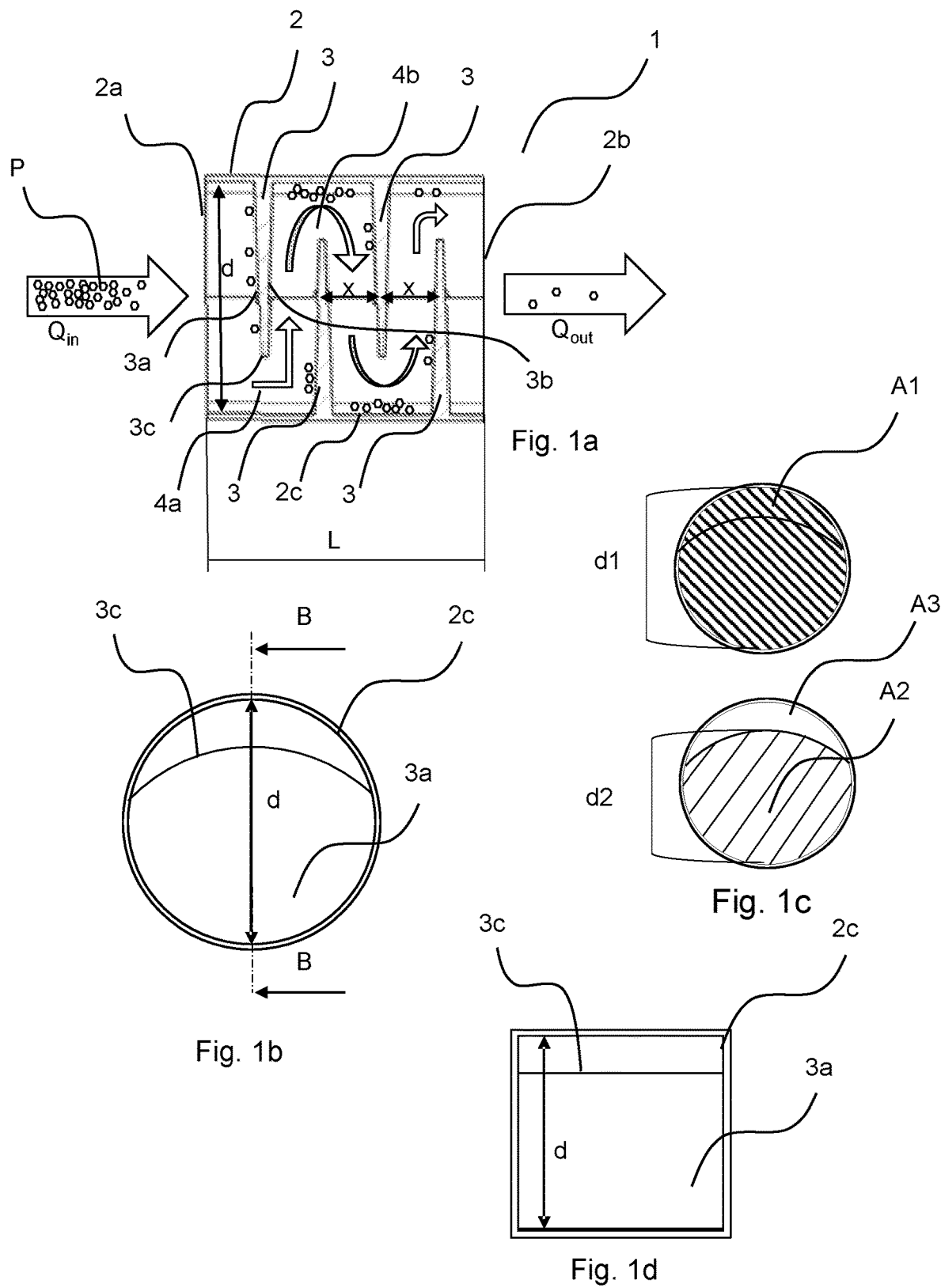

DEVICE FOR COLLECTING PARTICLES IN AN EXHALED AIR FLOW

CROSS-REFERENCE TO RELATED APPLICATIONS

This application is a continuation of U.S. non-provisional application Ser. No. 15/856,090, titled "A Device For Collecting Particles In An Exhaled Airflow" and filed on Dec. 28, 2017, which is a continuation of International Application No. PCT/EP2016/064110, filed Jun. 19, 2016, which claims the benefit of Swedish Patent Application No. SE 1550930-0, filed Jul. 1, 2015. The entire contents of all of the above-mentioned applications are hereby incorporated by reference.

TECHNICAL FIELD

The present invention relates generally to a device for collecting aerosol particles in an exhaled air flow. The particles may be aerosol particles consisting mainly of surfactant formed or found in the alveoli of the lungs, such as biomarkers or exogenous compounds containing traces of drugs or other substances.

BACKGROUND ART

Human breath contains aerosol particles that are formed from the respiratory tract lining fluid covering the airways during normal breathing. The particles have a size of between 0.1 and 2 µm, with an average size of between 0.3 and 0.8 µm. See article Characterization of Exhaled particles from the Healthy Human Lung, Journal of aerosol medicine and pulmonary drug delivery, Volume 23, Number 6, 2010 by Schwarz et al. The aerosol particles carry non-volatile components containing diagnostic information or biomarkers and are often studied as the breath condensate fraction. In this aerosol fraction, both lipids and peptides of endogenous origin have been demonstrated. It has also been discovered that exogenous compounds are present in the exhaled breath. Such exogenous compound may for example be drugs and narcotics. The respiratory tract lining fluid contain large quantities of antioxidants and surfactant. The surfactant phase is lipophilic and may represent a compartment for the exogenous compounds. Thus, exhaled breath can be used as a matrix for several types of testing such as for example testing of a medical condition or a medical treatment procedure, abused drug testing or doping testing. It can also be used for medical research.

With the discovery of exogenous aerosol particles consisting mainly of surfactant present in exhaled breath, a need for new methods and devices for collecting and analyzing the surfactant aerosol particles in exhaled breath has arisen. For accurate analysis it is of importance that as many of the aerosol particles as possible is collected from a sample breath. Further, in some applications, such as for example testing for drug abuse or doping, the collection of particles is performed away from a lab environment. However, there is a lack of methods and devices for easy collection of the aerosol particles in exhaled breath.

In prior art, for example in WO2009045163A1, it is described a device for collecting and sorting particles, indicative of a certain medical condition, in exhaled air. The device is an inertial impactor and comprises a housing with several partitions with a central opening. After each opening there is a collection plate which is arranged substantially perpendicular to the direction of flow of the gas stream. On the collection plates particles present in the flow of exhaled air are collected. The surface of the collection plates may be prepared with a surface treatment in order to optimize the collection of certain particles.

This impactor is a heavy and complex device, and the collection of particles need to take place in a lab, hospital or other controlled environment in order to ensure exact readings. Further, an impactor of this size needs a pump to draw the exhaled air through the device at a controlled rate. Further, the impactor only collects some of all particles present in the exhaled breath.

It is also previously known to collect aerosol particles in exhaled breath using different type of filters. In an article published in the Journal of Pharm Biomed Anal. 2011 Dec. 15; 56(5):1024-8. doi: 10.1016/j.jpba.2011.08.004 (Epub 2011 Aug. 9) with title "Demonstration that methadone is being present in the exhaled breath aerosol fraction" two type of filters are tested when collecting aerosol particles for analysis of methadone in exhaled breath. The two type of filters were a glass fiber filter and a polymer filter which where compared with an earlier used C18 silica filter. The polymer filter collected more than 90% of the aerosol particles in the exhaled breath. The polymer filter also has the practical advantage of having a low flow resistance making it possible to sample without pumping assistance. However, extracting the collected particles from a polymer filter is a complex process requiring a large amount of analysis fluid to separate the particles from the filter fibers.

Thus, there is a need to improve the prior art device for collecting biomarkers and other particles in exhaled air. Particularly, there is a need to provide a particle collector of such a size and simplicity that it can be used for sampling biomarkers, for example traces of drugs or medicine, in an on-site screening device or in a laboratory. The particle collector also needs to collect the majority of the particles present in the exhaled breath.

It is also an advantage if the particles collected are easily removed from the collector for analysis.

SUMMARY OF INVENTION

An object of the present invention is to create a small and simple but yet reliable and effective device for collecting aerosol particles, preferably aerosol particles consisting mainly of surfactant functioning as biomarkers, in exhaled breath. The device is described in the appended patent claims.

According to one embodiment of the invention a device for collecting aerosol particles in an exhaled airflow is provided, the device comprises
a housing having an extension direction between a first end with an inlet arranged to receive an exhaled airflow and a second end with an outlet arranged to transmit the exhaled airflow and an inner cross-section defined by inner walls of the housing arranged at a distance from each other,
at least four first type partition walls, arranged at a distance from each other and extending in a direction substantially perpendicular to the walls, partly covering the inner cross-section of the housing.
The device is characterized in that the first type partition walls protrude from opposite sides of the inner wall of the housing creating opposite openings between the first type partition walls and the housing inner wall, whereby the first type partition walls are arranged to create a labyrinth shaped flow path from the inlet to the outlet which is arranged to divert the air flowing from the inlet towards the outlet in a direction towards opposite inner wall of the housing so that the aerosol particles separate from the airflow and attach on the device, wherein the distance between two opposite first type partition walls is smaller than the distance between the inner walls of the housing.

When the airflow collides with a surface substantially perpendicular to the airflow the flow is diverted in a direction parallel to the surface. The diversion of the airflow separates the heavier aerosol particles in the exhaled air from the air itself. The heavier particles continue in the original flow direction and collide with and attaches to the partition walls or the housing inner wall, while the air changes direction and follow the labyrinth shaped flow path. Further, a direction change also creates a turbulent flow during which the particles are more easily separated from the air. Further, by making the distance between the partition walls smaller than the distance between the inner walls of the housing, i.e. decreasing the cross-sectional area of the flow path to constrict the flow, the speed of the exhaled air increases which in turn increases the amount of aerosol particles deposited/collected on the surfaces of the collecting device. Thus, a device according to the present invention collects a large number of aerosol particles in the exhaled breath, yet has a flow resistance so low that a person is able to breathe through the device without the use of a separate pump drawing exhaled breath from the person.

In one embodiment, each first type partition wall has a partition area substantially parallel to the extension direction of the housing, covering 50-95%, preferably 60-85%, more preferably 65-80% of the inner cross-section area of the housing.

When the first type partition wall covering 50-95%, preferably 60-85%, more preferably 65-80% of the inner cross-section of the housing, an opening is created between the first type partition and the housing inner wall having an area large enough to not create a too high flow resistance yet an area small enough to create an acceleration of the airflow creating a turbulent flow.

In one embodiment, the inner cross-section area is between 20 $mm^2$ and 615 $mm^2$, preferably between 50 and 250 $mm^2$, most preferably between 70 and 90 $mm^2$.

In one embodiment the opening area is within the interval of 10 $mm^2$-25 $mm^2$, the extension length between 10 and 70 mm and the number of first type partition walls between 4 and 14.

A device having the above-mentioned specifications enable a certain pressure difference over the device, creating a flow velocity through the device which is high to separate the particles from the airflow without creating a too high counter pressure.

In one embodiment, the at least four first type partition walls are arranged separated with a constant distance.

A collector according to this embodiment have a production advantage since it can be made symmetrical.

In another embodiment, the first type partition walls are arranged separated with an increasing distance in the flow direction.

A particle collection device having an increasing distance between the first type partition walls closer to the outlet, create less flow resistance to the air flow. This since the air having travelled some path though the device loose velocity and by arranging the partition walls further apart with the airflow is slower, the slower airflow near the outlet do not have to make as many direction changes as the airflow near the inlet, thus decreasing the resistance of the flow.

In one embodiment, the housing comprises at least one second type partition wall arranged substantially parallel to the extension direction of the housing. In one embodiment, the housing comprises at least two second type partition walls which are arranged parallel to each other.

By adding at least one second type of partition wall to the device the impact area of the aerosol particles is increased, and more particles are possible to collect without substantially increasing the flow resistance.

In one embodiment, the at least one second type partition wall extend from the inlet to the outlet of the housing.

When the second type partition wall or walls extend all the way from the inlet to the outlet, at least two flow channels are created guiding the flow from the inlet to the outlet. The flow channels may in one embodiment be arranged to have the same flow resistance by adapting the design of the outer edge of the first type partition wall, thus the opening flow area, to the position of the second type partition walls.

In one embodiment, the housing has the shape of an elongated cylinder.

When the housing has the shape of a cylinder the device can easily be fitted into a test tube for analysis. The test tube may comprise any type of analysis fluid of an amount covering at least a part of, but preferably the entire length of the device. The analysis fluid is adapted to wash away the collected aerosol particles from the device and may in a later analysis step be analyzed to determine presence and type of aerosol particles collected.

In one embodiment, the device is made of a non-absorbent material, for example polypropylene (PP), polyvinylidene fluoride (PVDF), polytetrafluoroethylene (PTFE), fluorinated ethylene propylene (FEP) or other non-absorbent, preferably, polymer materials.

If a non-absorbent material specified as above is used, the material is approved for medical purposes and the aerosol particles attached on the device is easily washed off for a later analysis.

In one embodiment, at least one of the following parts have a rough surface structure in order to increase surface area; housing, first type partition walls, second type partition wall.

If the device is provided with a rough structure on at least a part of its surface the surface area increases, and the number of particles collected can be increased.

In one embodiment, the device comprises a first and a second housing half which are adapted to be joined.

When the device is designed to be constructed out of two, preferably identical, halves the production process is simplified. By dividing the device in two, each partition walls and possible rough structure on the inner wall can be easily produced by using a cutting production tool. It is also possible to produce two identical halves of which one is turned 180 degrees before joining.

In one embodiment, each housing half comprises at least two first type partition walls extending further than half of the total cross-section of the housing.

If each first type partition wall shall cover covering 50-95%, preferably 60-85%, more preferably 65-80% of the total cross-section area of the housing, as stated in one embodiment above, the first type partition in each housing half must extend further than half of the total cross-section of the housing.

In one embodiment, each housing half comprises at least one second type partition wall arranged substantially parallel to the extension direction of the housing extending a maximum of half of the total cross-section of the housing.

To enable joining of the two halves the second type partition wall may not protrude further than half of the total cross-section of the housing.

In one embodiment, the at least one second type partition wall have at least two recesses in which the at least two first type partitions are arranged to be inserted.

In order for the first type partition walls to be able to extend further than half of the total cross-section of the housing, the second type partition walls have in this embodiment cuttings which are adapted to receive the outer ends of the first type partition walls. The first type partition walls may in one embodiment be arranged to be inserted by press fitting into the cuttings. A press fit also have the advantage of acting like a glue, joining the two device halves.

In one embodiment, the particles in exhaled airflow are biomarkers, such as pulmonary surfactant, drugs or other endogenous or exogenous compounds found in the alveoli of the lungs having a size of between 0.1 and 2 µm, with an average size of between 0.3 and 0.8 µm.

Aerosol particles in the form of biomarkers or particles related to drugs or other exogenous compounds are the most interesting particles arranged to be collected by this device. The particles have an average size of between 0.3 and 0.8 µm. Larger particles such as saliva or other particles will to a large extent be collected on the first type partition wall which is arranged closest to the inlet, i.e. closest to the mouth of the person exhaling into the device. Smaller and lighter particles will to a large extent follow the airflow and exit the device through the outlet.

BRIEF DESCRIPTION OF DRAWINGS

The invention is now described, by way of example, with reference to the accompanying drawings, in which:

FIG. 1a show a cut view of one embodiment of the invention.

FIG. 1b show a plane view of the embodiment shown in FIG. 1a.

FIG. 1c visualizes the different areas defining the invention

FIG. 1d shown a different embodiment of the invention having a different cut section geometry.

FIG. 2b show a plane view of the embodiment shown in FIG. 2a.

FIG. 3 show a plane view of another embodiment of the invention.

DESCRIPTION OF EMBODIMENTS

Figure 2A:
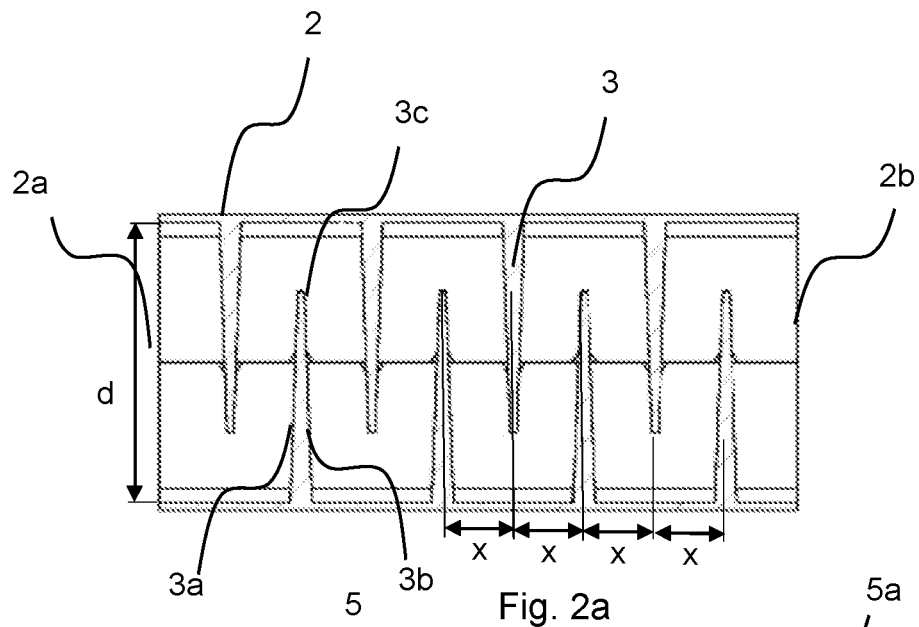
FIG. 2a show a cut view of one embodiment of the invention.
Figures 2B, 3:
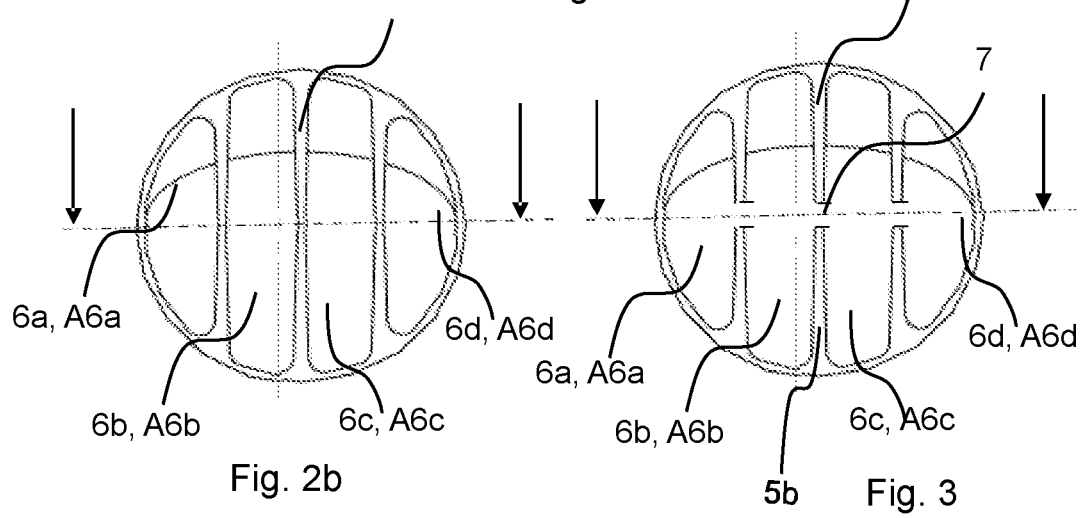

In the following, a detailed description of device according to the invention is presented. In the drawing figures, like reference numerals designate identical or corresponding elements throughout the several figures. It will be appreciated that these figures are for illustration only and are not in any way restricting the scope of the invention.

FIGS. 1a and 1b disclose an embodiment of the device 1 for collection particles in exhaled breath. FIG. 1a is a cut view taken at cut B-B in FIG. 1b and show the inside of the device 1. FIG. 1c visualizes the different cross-section areas of the invention. FIG. 1d is another cut view of another embodiment of the device.

The device 1 comprises a housing 2 having an extension direction between a first end 2a with an inlet and a second end 2b with an outlet. The inlet is arranged to receive an exhaled airflow $Q_{in}$ comprising aerosol particles P from a subject, such as for example a person, and the outlet is arranged to transmit the exhaled airflow $Q_{out}$ from the device 1. Thus, the exhaled air is arranged to flow in a direction from the inlet to the outlet. The housing 2 has an inner cross-section area A1 defined by inner walls 2c of the housing 2. In the embodiment shown in FIG. 1a-1c the housing has an elongated cylindrical shape with a length L and a circular cross-section, i.e. the cross-section area A1 has an area defined by the inner diameter d1 of the housing 2. FIG. 1d disclose another embodiment of the invention where the housing has a rectangular cross-section and the cross-section area A1 is defined by the height and width of the housing. Other cross-section area shapes are also possible, but the cross-section area is always defined by the distance d between the inner walls 2c of the housing.

The outer diameter of the housing is in one embodiment of such a dimension that it can easily be fitted into a standard size test tube. I.e. it has a diameter between 8 and 30 mm, preferably between 10 and 20 mm. The inner cross-section area A1 is therefore slightly less than the above-mentioned area, depending on the thickness of the housing walls. Therefore, the cross-section area A1 may be between 20 mm² and 615 mm², preferably between 50 and 250 mm², most preferably between 70 and 90 mm². Comparably, the distance d between the inner walls 2c of the housing may be between 5 and 28 mm, preferably between 8 and 18 mm, most preferably between 9.5 and 10.5 mm.

At least four partition walls of a first type 3 are arranged to extend in a direction substantially perpendicular to the inner walls 2c, thus substantially perpendicular to the initial direction of the exhaled airflow when exiting the subject's mouth. Each first type partition wall 3 has a first surface 3a facing the air flow, an opposite second surface 3b and a peripheral edge 3c. The first and second surface 3a and 3b each have a surface area A2 smaller than the cross-section area A1. Thus, the first type partition walls have a surface area A2 partly covering the inner cross-section area A1 of the housing 2. In different embodiments the first type partitions walls have a surface area A2 covering 50-95%, preferably 60-85%, more preferably 65-80% of the cross-section area A1.

The first type partition walls 3 protrude from opposite sides of the inner wall 2c of the housing 2. Thus, the walls are creating opposite openings 4a, 4b between the first type partition walls 3 and the housing inner wall 2c having an opening area A3=A1−A2.

The first type partition walls 3 are arranged to create a labyrinth shaped flow path having a cross-sectional flow area from the inlet to the outlet. When the airflow collides with a surface substantially perpendicular to the air flow, the flow is diverted in a direction parallel to the surface. The diversion of the airflow separates the heavier particles P in the exhaled air from the air itself. The heavier particles P continue in the original flow direction and collide with the partition walls 3 or the housing inner wall 2a, while the air changes direction and follow the labyrinth shaped flow path. The longer distance the air flows and the more and larger direction changes the airflow is forced to do, the larger number of particles are separated from the air and collected in the device 1. Further, a direction change also creates a turbulent flow during which the particles are more easily separated from the air. A turbulent air also increases the impact frequency between the particles and the surfaces of the walls of the device 1, thus increasing the amount of airborne particles P attaching to the surfaces. Thus, the outflow $Q_{out}$ out of the device comprises less particles P than the inflow $Q_{in}$ into the device.

A person is only able to exhale with a certain maximum flow rate $Q_{in}$. At a certain counter pressure from the device the velum of the person closes, and exhalation is impossible. The pressure difference over the device must therefore not be too high. However, a certain inflow $Q_{in}$ and pressure difference is necessary to create the certain conditions with a high enough flow velocity to separate the particles from the air flow. It is therefore important to design the device to have a certain flow path cross-sectional flow area which is defined by a first cross-sectional flow area, defined by the opening area A3 between the first type partition walls 3 and the inner walls of the housing and a second cross-sectional flow area circumscribed by the first type partition walls and the inner diameter d1 of the housing. I.e. the parameters defining the second cross-sectional flow area are the specific extension length L of the housing, the distance d between the inner walls 2*c* of the housing or inner diameter d1 of the housing and the number of first type partition walls 3 of the device 1, i.e. the distance x between the first type partition walls 3. The opening area A3 is preferably within the interval of 10 $mm^2$-25 $mm^2$, the extension length L between 10 and 70 mm and the number of first type partition walls 3 between 4 and 14. The first cross-sectional flow area is in one embodiment smaller than the second cross-sectional flow area. This relationship increases the acceleration of the air flowing pass the peripheral edge 3*c* of the first type partition wall 3.

In the preferred embodiment shown for example in FIG. 2*a* the number of first type partition walls 3 are 8, the length L approximately 22 mm and the area A3 is approximately 20 $mm^2$. Thus, in this embodiment the wall surface area A2 cover approximately 75% of the total inner cross-section area A1.

In order to increase the flow area, it is in one embodiment of the invention possible to arrange more than one device parallel to each other in an additional outer housing (not shown) thus decreasing the total flow resistance.

The first type partition walls 3 may be separated from each other with a certain distance x depending on the maximum allowed pressure difference over the device. The distance x depends on the length L of the device and the number of first type walls 3. However, in order to create the certain conditions with a high enough flow velocity to separate the aerosol particles from the air flow, the distance x between at least two opposite first type partition walls 3 is always smaller than the distance d between the inner walls of the housing. In one embodiment, shown in FIGS. 1*a* and 2*a* the distance x is constant. In another embodiment, show in FIG. 4, the distance between the first type partition walls 3 is increasing in the distance from the first end 2*a* of the device 1. I.e. the distance $x_1$ between the two opposite partition walls 3 closest to the inlet 2*a* is smaller than the distance $x_n$ between the two opposite partition walls 3 closest to the outlet 2*b*. With an increasing distance between the first type partition walls 3 the flow velocity through the device 1 can be substantially maintained. In the embodiment shown in FIG. 4, the second flow path cross-sectional flow area is increasing towards the outlet 2*b* due to the increasing distance between the first type partition walls and the constant kept opening area A3. However, it is also possible to gradually increase the opening area A3 closer to the outlet 2*b*. This will further decrease the flow resistance in the device and contribute to a maintained flow velocity. In one embodiment, the relation between the first flow path cross-sectional flow area and the second flow path cross-sectional flow area is kept substantially constant throughout the entire length L of the device.

In one embodiment, see FIG. 1*b*, the openings 4*a*, 4*b* have the shape of circle segments, wherein the cord delimiting the circle segment is defined by the peripheral edge 3*c* of the first type partition wall. The peripheral edge 3*c* may be arranged as a straight line, see FIG. 1*d*, or may be have an arc shape, see FIGS. 1*b*, 1*c*, 2*b* and 3.

The device is in one embodiment made of a non-absorbent material, for example polymer materials such as for example polypropylene (PP), polyvinylidene fluoride (PVDF), polytetrafluoroethylene (PTFE), fluorinated ethylene propylene (FEP) or other non-absorbent, preferably, polymer materials. On a non-absorbent material the particles may attach but are easily washed off when a later analyzing step is performed. The washing off may be performed in a test tube filled with an amount of test fluid enough to cover the entire length L of the housing.

In order to increase the surface area on which the particles P are collected, the housing inner wall have in one embodiment a rough surface structure. The rough structure is in one embodiment adapted to the size of the particles to be collected. I.e. if the aerosol particles to be collected have a diameter of 0.1 and 2.0 μm the inner walls may preferably be provided or covered with cavities of approximately the same size. The surface may also be machined to have protrusions distanced by approximately the same distance as the diameter of the particles. The rough structure may also for example be a spark or electro eroded surface with a surface roughness Ra from 0.1 micron to up to 12.5 micron. The possible surface roughness value also depend on the draft angle on the surface to be eroded in relation to the tool producing the eroded surface. With a larger draft angle, a larger surface roughness is possible to create.

It is also possible to further increase the surface area by providing all surfaces of the device, both inner and outer with a rough structure. Different surface roughness values are possible on different surfaces of the device 1.

In one embodiment the first surface 3*a* and second surface 3*b* of the first type partition walls 3 are directed at an angle in relation to each other such that the edge 3*c* of the respective first type wall 3 is narrower than the base of the first type wall. However, the first surface 3*a* and second surface 3*b* of the first type partition walls 3 may also be parallel or substantially parallel to each other, as can been seen in FIG. 3. They may also be produced having only a small draft angle.

FIGS. 2*b* and 2*c* and FIGS. 4*a*-*e* show another embodiment where the housing further comprises at least one second type partition wall 5. The second type partition wall 5 is arranged substantially parallel to the extension direction of the housing 2. The at least one second type partition wall 5 extend from the first end 2*a* to the second end 2*b* of the housing creating at least two flow channels 6*a*-6*d* leading the airflow from the inlet to the outlet. In the embodiment according to FIGS. 2*b*, 2*c* and FIGS. 4*a*-*e* three second type parallel partition walls 5 are shown thus four flow channels 6*a*-6*d* are created. The flow channels 6*a*-6*d* have, in the embodiment shown in FIGS. 2*b* and 2*c*, different flow areas A6*a*-A6*d*. Thus, a pressure change may occur in the different channels creating different flow velocities through the different channels.

In FIG. 3 another embodiment is show where the second type partition wall or walls 5 are divided into two wall parts 5*a*, 5*b* protruding from opposite sides of the inner wall 2*c* of the housing 2 so that a small gap 7 is arranged between the two wall parts 5a, 5b. The small gap 7 compensate for the pressure changes which may occur in the channels 6a-6d. The gap also contributes to a turbulent airflow in the channels.

Figure 4:
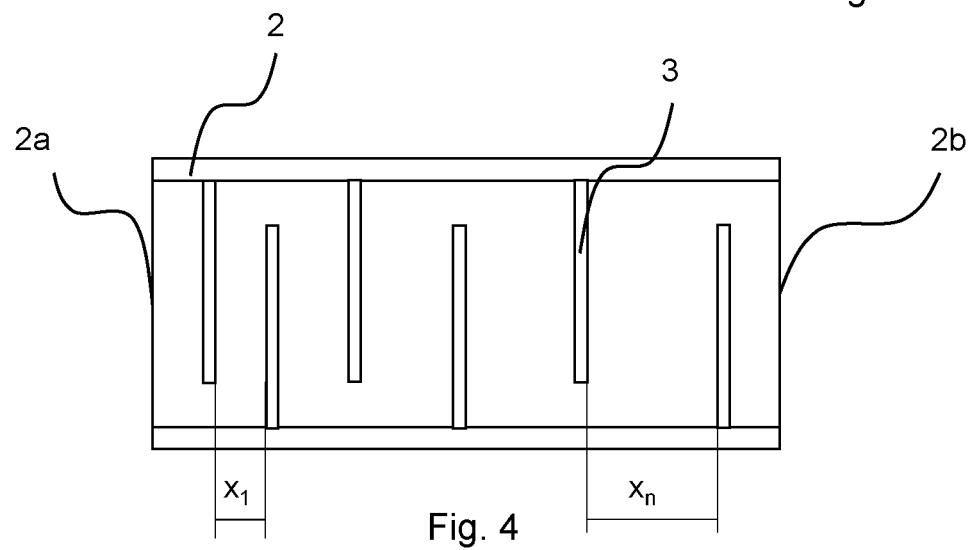
FIG. 4 show a cut view of yet another embodiment of the invention.
Figure 5A:
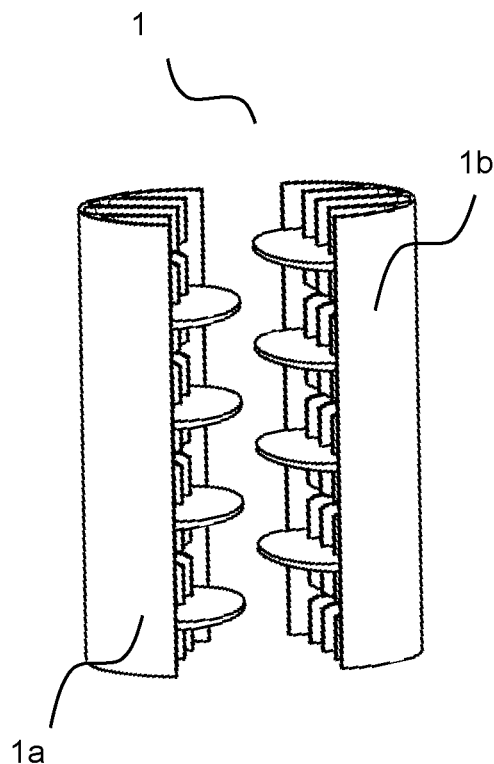
FIG. 5a-5d show yet another embodiment of the invention.
Figure 5B:
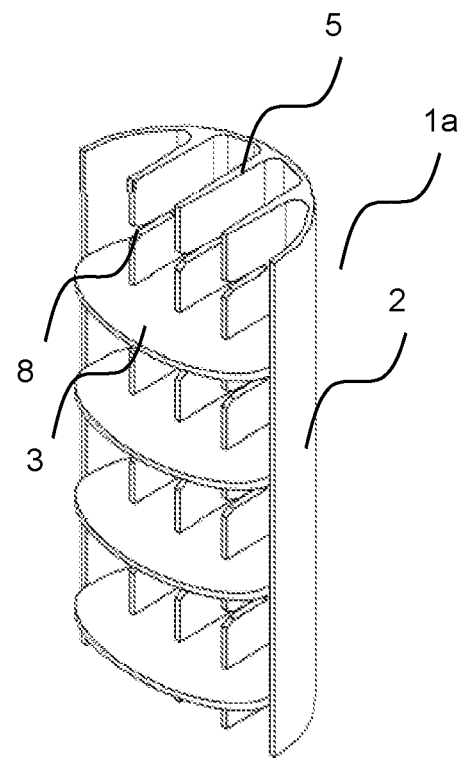
Figure 5C:
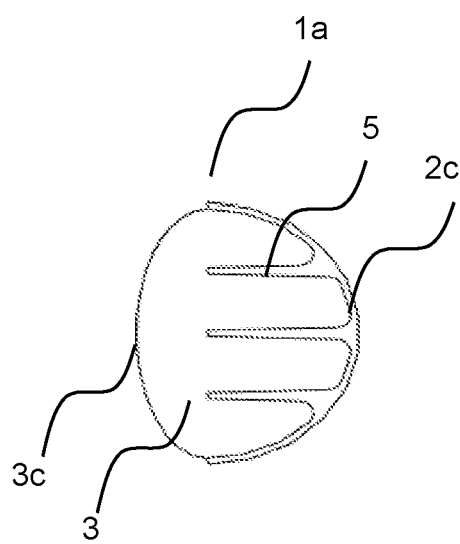
Figure 5D:
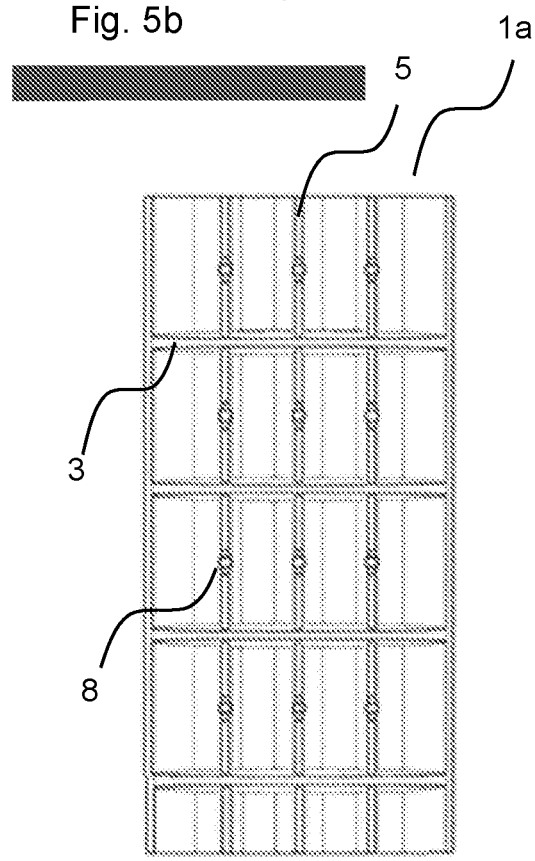

According to one embodiment, shown in FIGS. 5a-5d, the device 1 comprises two device halves 1a, 1b which are adapted to be joined. When the device part 1a and 1b according to FIG. 4a-4d are joined they together form an elongated cylinder with a total cross-section area A1. Each device half 1a, 1b comprises at least two first type partition walls 3 extending further than half of the total cross-section A1 of the housing 2. In one embodiment the first type partition walls 3 extend between 10% and 60% further than half of the total cross-section A1 of the housing 2.

Each housing half 1a, 1b comprises at least one partition wall of a second type 5 arranged substantially parallel to the extension direction of the housing 1 extending a maximum of half the total cross-section of the housing 1. In order for the first type partition walls 3 to be able to extend further than half of the total cross-section A1 of the housing 2 the second type partition walls 5 have cuttings 8 which are adapted to receive the outer ends 3c of the first type partition walls. The first type partition walls 3 are in one embodiment arranged to be inserted by press fitting into the cuttings 8.

A preferred embodiment of a device 1 for collecting particles according to the invention has been described. However, the person skilled in the art realizes that this can be varied within the scope of the appended claims without departing from the inventive idea.

All the described alternative embodiments above or parts of an embodiment can be freely combined without departing from the inventive idea as long as the combination is not contradictory.

The invention claimed is:

1. A device for collecting aerosol particles in an exhaled airflow, the device comprising:
   a housing having an extension length in a direction between a first end with an inlet arranged to receive an exhaled airflow and a second end with an outlet arranged to transmit the exhaled airflow, and an inner cross-section defined by one or more inner walls of the housing, wherein the cross-section exhibits a transverse width, and wherein the housing has an elongated shape; and
   at least four first type partition walls, arranged at a distance from each other and extending in a direction substantially perpendicular to the inner wall, partly covering the inner cross-section of the housing,
   wherein the first type partition walls protrude from opposite sides of the one or more inner walls of the housing creating opposite openings with an opening area between the first type partition walls and the respective opposite inner wall of the housing, whereby the first type partition walls are arranged to create a labyrinth shaped flow path from the inlet to the outlet which is arranged to divert the air flowing from the inlet towards the outlet in a direction towards the opposite inner wall of the housing so that the aerosol particles separate from the airflow and attach on the device;
   wherein the distance between two opposite first type partition walls is smaller than the transverse width of the cross section; and
   wherein the distance between opposite first type partition walls increases in the extension direction of the housing from the inlet.

2. The device according to claim 1, wherein each first type partition wall has a partition area substantially perpendicular to the extension direction of the housing, covering 50-95% of the inner cross-section area of the housing.

3. The device according to claim 1, wherein the inner cross-section area is between 20 $mm^2$ and 615 $mm^2$.

4. The device according to claim 1, wherein the opening area is within the interval of 10 mm-25 $mm^2$, the extension length between 10 and 70 mm and the number of first type partition walls between 4 and 14.

5. The device according to claim 1, wherein the housing has the shape of an elongated cylinder with a circular cross-section.

6. The device according to claim 5, wherein the housing has a diameter between 8 and 30 mm.

7. The device according to claim 1, wherein the housing has a rectangular cross-section.

8. The device according to claim 1, wherein the device is made of a non-absorbent material.

9. The device according to claim 1, wherein at least one of the following parts has a rough surface structure in order to increase surface area: housing, first type partition walls.

10. The device according to claim 1, wherein the housing comprises a first and a second housing half which are adapted to be joined.

11. The device according to claim 10, wherein each housing half comprises at least two first type partition walls extending further than half of the total cross-section of the housing.

12. The device according to claim 11, wherein each housing half comprises at least one second type partition wall arranged substantially parallel to the extension direction of the housing extending a maximum of half of the total cross-section of the housing.

13. The device according to claim 12, wherein the at least one second type partition wall has at least two recesses in which the at least two first type partition walls are arranged to be inserted.

14. The device according to claim 12, wherein the at least one second type partition wall has a rough surface structure in order to increase surface area.

15. The device according to claim 1, wherein the opening area between the first type partition walls and the respective opposite inner wall of the housing gradually increases in the extension direction of the housing from the inlet.

16. The device according to claim 1, wherein the opening area defines a first cross-sectional flow area, and the first type partition walls and the transverse width of the cross-section of the housing defines a second cross-sectional flow area, wherein the relation between the first cross-sectional flow area and the second cross-sectional flow area is kept essentially constant throughout the entire length of the device.

* * * * *